(12) United States Patent
Takei (10) Patent No.: US 11,915,414 B2
(45) Date of Patent: Feb. 27, 2024

(54) MEDICAL IMAGE PROCESSING APPARATUS, METHOD, AND PROGRAM

(71) Applicant: FUJIFILM Corporation, Tokyo (JP)

(72) Inventor: Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 361 days.

(21) Appl. No.: 17/161,703

(22) Filed: Jan. 29, 2021

(65) Prior Publication Data

US 2021/0150713 A1 May 20, 2021

Related U.S. Application Data

(63) Continuation of application No. PCT/JP2019/026533, filed on Jul. 3, 2019.

(30) Foreign Application Priority Data

Sep. 14, 2018 (JP) .................................. 2018-172989

(51) Int. Cl.
*G06T 7/00* (2017.01)
*G16H 50/20* (2018.01)
(Continued)

(52) U.S. Cl.
CPC .......... *G06T 7/0012* (2013.01); *A61B 5/0042* (2013.01); *G06N 3/045* (2023.01);
(Continued)

(58) Field of Classification Search
CPC ......... G06T 7/0012; G06T 2207/10081; G06T 2207/20081; G06T 2207/20084;
(Continued)

(56) References Cited

U.S. PATENT DOCUMENTS

2006/0110036 A1 5/2006 Luo et al.
2011/0176710 A1* 7/2011 Mattiuzzi .............. G06T 7/0012
382/128

(Continued)

FOREIGN PATENT DOCUMENTS

CN 107292884 10/2017
JP H08251404 9/1996
(Continued)

OTHER PUBLICATIONS

"Office Action of Japan Counterpart Application", dated Apr. 12, 2022, with English translation thereof, p. 1-p. 8.
(Continued)

*Primary Examiner* — Van D Huynh
(74) *Attorney, Agent, or Firm* — JCIPRNET (57) ABSTRACT

A discrimination unit discriminates a disease region included in a medical image. The discrimination unit has a first neural network which discriminates a first medical feature in the medical image, and consists of a plurality of processing layers, and a second neural network which discriminates a second medical feature associated with the first medical feature, in the medical image, and consists of a plurality of processing layers. A feature quantity output from the processing layer in the middle of the second neural network or an output result of the second neural network is input to the first neural network.

9 Claims, 4 Drawing Sheets (51) Int. Cl.
*A61B 5/00* (2006.01)
*G06N 3/08* (2023.01)
*G06N 3/045* (2023.01)

(52) U.S. Cl.
CPC ............... *G06N 3/08* (2013.01); *G16H 50/20* (2018.01); *G06T 2207/10081* (2013.01); *G06T 2207/20081* (2013.01); *G06T 2207/20084* (2013.01); *G06T 2207/30016* (2013.01)

(58) Field of Classification Search
CPC ........ G06T 2207/30016; A61B 5/0042; A61B 5/055; A61B 6/03; G06N 3/045; G06N 3/08; G06N 3/044; G16H 50/20; G16H 30/40; G01T 1/161
USPC ........................................................ 382/128
See application file for complete search history.

(56) References Cited

U.S. PATENT DOCUMENTS

| | | | | |
|---|---|---|---|---|
| 2017/0236027 | A1* | 8/2017 | van der Made | G06V 10/82 382/158 |
| 2017/0287134 | A1* | 10/2017 | Abedini | G06T 7/149 |
| 2018/0068218 | A1* | 3/2018 | Yoo | G06V 10/82 |
| 2018/0075628 | A1* | 3/2018 | Teare | G06F 18/24143 |
| 2018/0365824 | A1* | 12/2018 | Yuh | G06F 18/2431 |

FOREIGN PATENT DOCUMENTS

| | | |
|---|---|---|
| JP | 2008520391 | 6/2008 |
| JP | 2009512528 | 3/2009 |
| JP | 2016031747 | 3/2016 |
| KR | 20180025093 | 3/2018 |
| WO | 2017106645 | 6/2017 |
| WO | 2018026431 | 2/2018 |

OTHER PUBLICATIONS

"International Search Report (Form PCT/ISA/210) of PCT/JP2019/026533," dated Oct. 1, 2019, with English translation thereof, pp. 1-5.

"Written Opinion of the International Searching Authority (Form PCT/ISA/237) of PCT/ JP2019/026533," dated Oct. 1, 2019, with English translation thereof, pp. 1-9.

"Search Report of Europe Counterpart Application", dated Oct. 8, 2021, pp. 1-11.

"Office Action of Japan Counterpart Application" with English translation thereof, dated Jan. 11, 2022, p. 1-p. 9.

"Office Action of Japan Counterpart Application", dated Feb. 28, 2023, with English translation thereof, p. 1-p. 15.

* cited by examiner

MEDICAL IMAGE PROCESSING APPARATUS, METHOD, AND PROGRAM

CROSS REFERENCE TO RELATED APPLICATIONS

The present application is a Continuation of PCT International Application No. PCT/JP2019/026533 filed on Jul. 3, 2019, which claims priority under 35 U.S.C. § 119(a) to Japanese Patent Application No. 2018-172989 filed on Sep. 14, 2018. Each of the above applications is hereby expressly incorporated by reference, in its entirety, into the present application.

BACKGROUND

Technical Field

The present disclosure relates to a medical image processing apparatus, and a medical image processing method, and a medical image processing program which discriminate medical features included in a medical image such as a computed tomography (CT) image of a head.

Related Art

In recent years, with advances in medical equipment such as CT devices and magnetic resonance imaging (MRI) devices, an image diagnosis using high resolution medical images having higher quality can be performed. In particular, in a case where a target part is a brain, since it is possible to specify a disease region causing vascular disorders such as cerebral infarction and cerebral hemorrhage, by the image diagnosis using CT images and MRI images, an appropriate treatment can be performed on the basis of the specified result. In general, the disease region shows a higher CT value on the CT image as compared with the surrounding region. Therefore, it is possible to discriminate a disease region by interpreting the presence or absence of a region showing a higher CT value as compared with the surrounding region in the image diagnosis.

In this manner, various methods for automatically discriminating the disease region from the medical image have been proposed. For example, in JP1996-251404A (JP-H08-251404A), a discrimination device has been proposed which comprises first and second neural networks having an input layer, an intermediate layer, and an output layer, and in which the first and second neural networks are combined such that the output from the input layer to the intermediate layer of the first neural network is input to the input layer of the second neural network. In the discrimination device disclosed in JP1996-251404A (JP-H08-251404A), a discrimination result for region attributes of image data is output on the basis of the image data input to the first neural network. By using such a discrimination device, it is possible to discriminate specific medical features included in the medical image as described above.

However, in some cases, depending on the types of the medical features, it is difficult to discriminate the medical feature from the medical image.

SUMMARY OF THE INVENTION

The present disclosure is made in view of such circumstances, and an object thereof is to make it possible to easily discriminate the medical features from the medical image.

A medical image processing apparatus according to an aspect of the present disclosure comprises a discrimination unit that discriminates a region of a first medical feature included in a medical image, in which the discrimination unit has a first neural network which discriminates the first medical feature in the medical image, and consists of a plurality of processing layers, and a second neural network which discriminates a second medical feature associated with the first medical feature, in the medical image, and consists of a plurality of processing layers, and a feature quantity output from the processing layer in the middle of the second neural network or an output result of the second neural network is input to the first neural network.

The term "discriminating" includes both discriminating the presence or absence of the first or second medical feature in the medical image and discriminating a location of the first or second medical feature in the medical image.

The feature quantity output from the processing layer in the middle of the second neural network or the output result of the second neural network may be input to the processing layer in the middle of the first neural network, or may be input to the first processing layer in the first neural network.

In the medical image processing apparatus according to the aspect of the present disclosure, the second neural network may have learned a task different from the first neural network.

In the medical image processing apparatus according to the aspect of the present disclosure, the task learned by the second neural network may be any one of a task to predict presence or absence of a disease, a task to predict a type of a disease, a task to predict clinical findings expressed in a patient, or a task to predict an awareness level of a patient.

In the medical image processing apparatus according to the aspect of the present disclosure, the first neural network may discriminate a local medical feature from the medical image, as the first medical feature, and the second neural network may discriminate a global medical feature from the medical image, as the second medical feature.

In the medical image processing apparatus according to the aspect of the present disclosure, the medical image may include a brain, the local medical feature may be at least one of a bleeding region or an infarction region of the brain, and the global medical feature may be presence or absence of the at least one of the bleeding region or the infarction region.

The medical image processing apparatus according to the aspect of the present disclosure may further comprise a display controller that displays the medical image in which the local medical feature is specified, on a display unit.

In the medical image processing apparatus according to the aspect of the present disclosure, the medical image may be a CT image of a brain.

A medical image processing method according to another aspect of the present disclosure is a medical image processing method of discriminating a region of a first medical feature included in a medical image using a discrimination unit, in which the discrimination unit has a first neural network and a second neural network, and a feature quantity output from a processing layer in the middle of the second neural network or an output result of the second neural network is input to the first neural network, and the medical image processing method includes discriminating the first medical feature in the medical image using the first neural network; and discriminating a second medical feature associated with the first medical feature, in the medical image using the second neural network.

A program for causing a computer to execute the medical image processing method according to the aspect of the present disclosure may be provided.

A medical image processing apparatus according to another aspect of the present disclosure comprises a memory that stores a command for causing a computer to execute a process of discriminating a region of a first medical feature included in a medical image using a discrimination unit, and a processor configured to execute the stored command, in which the processor functions as the discrimination unit that has a first neural network and a second neural network, in which a feature quantity output from a processing layer in the middle of the second neural network or an output result of the second neural network is input to the first neural network, and the processor executes a process of discriminating the first medical feature in the medical image using the first neural network, and discriminating a second medical feature associated with the first medical feature, in the medical image using the second neural network.

According to the present disclosure, it is possible to easily and accurately discriminate the first medical feature in the medical image.

DETAILED DESCRIPTION

Figure 1:
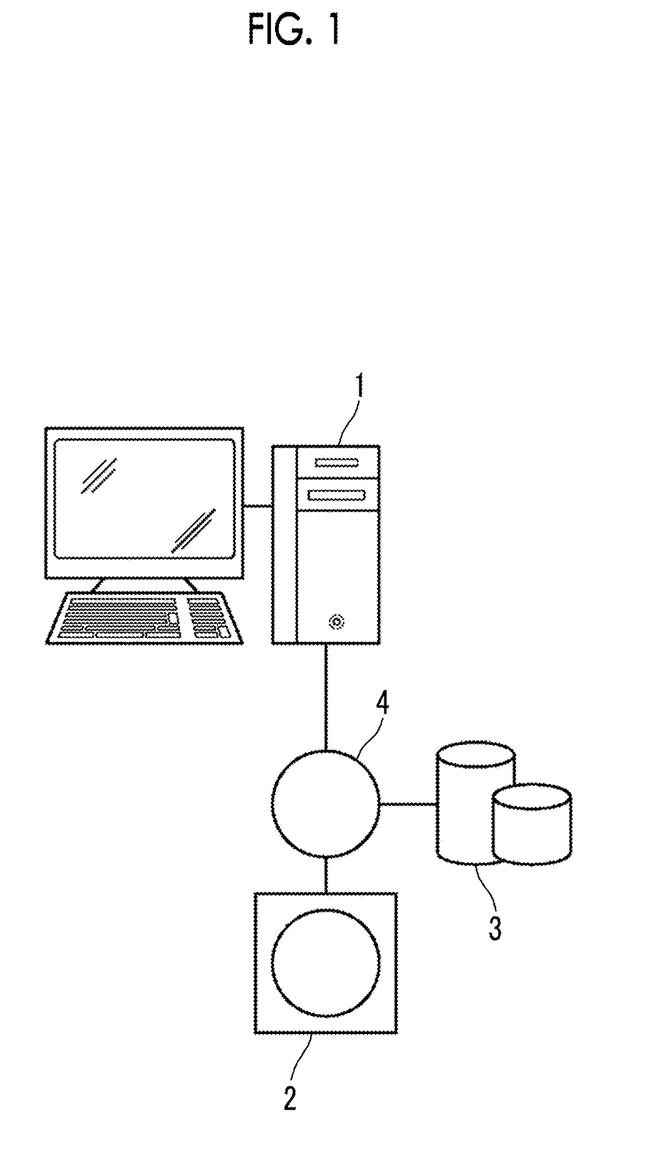
FIG. 1 is a hardware configuration diagram illustrating an outline of a diagnosis support system to which a medical image processing apparatus according to an embodiment of the present disclosure is applied.

Hereinafter, embodiments of the present disclosure will be described in detail with reference to the drawings. FIG. 1 is a hardware configuration diagram illustrating an outline of a diagnosis support system to which a medical image processing apparatus according to an embodiment of the present disclosure is applied. As illustrated in FIG. 1, in the diagnosis support system, a medical image processing apparatus 1 according to the embodiment, a three-dimensional image capturing device 2, and an image storage server 3 are connected via a network 4 in a communicable state.

The three-dimensional image capturing device 2 is a device that images a part as a diagnosis target of a subject to generate a three-dimensional image representing the part, and specifically, is a CT device, an MRI device, a positron emission tomography (PET) device, or the like. The three-dimensional image generated by the three-dimensional image capturing device 2 is transmitted to the image storage server 3 to be saved. In the embodiment, the diagnosis target part of the patient as the subject is a brain, the three-dimensional image capturing device 2 is a CT device, and a CT image of a head including the brain of the subject is generated as a three-dimensional brain image BO.

The image storage server 3 is a computer that saves and manages various kinds of data, and comprises a large-capacity external storage device and software for database management. The image storage server 3 performs communication with other devices via the network 4 in a wired or wireless manner, and transmits and receives various kinds of image data. Specifically, the various kinds of data including the image data of the brain image BO generated by the three-dimensional image capturing device 2 are acquired via the network, and are saved and managed in a recording medium such as a large-capacity external storage device. The image data storage format and the communication between the devices via the network 4 are based on the protocol such as Digital Imaging and Communication in Medicine (DICOM).

The medical image processing apparatus 1 is obtained by installing a medical image processing program of the embodiment in one computer. The computer may be a workstation or a personal computer that a doctor performing a diagnosis operates directly, or a server computer connected to the workstation or personal computer via a network. The medical image processing program is distributed by being recorded in a recording medium such as a digital versatile disc (DVD) and a compact disc read only memory (CD-ROM), and is installed to a computer from the recording medium. Otherwise, the medical image display program may be stored in a storage device of a server computer connected to a network or a network storage in a state of being accessible from the outside, and be downloaded and installed in a computer that the doctor uses, in response to the request.

Figure 2:
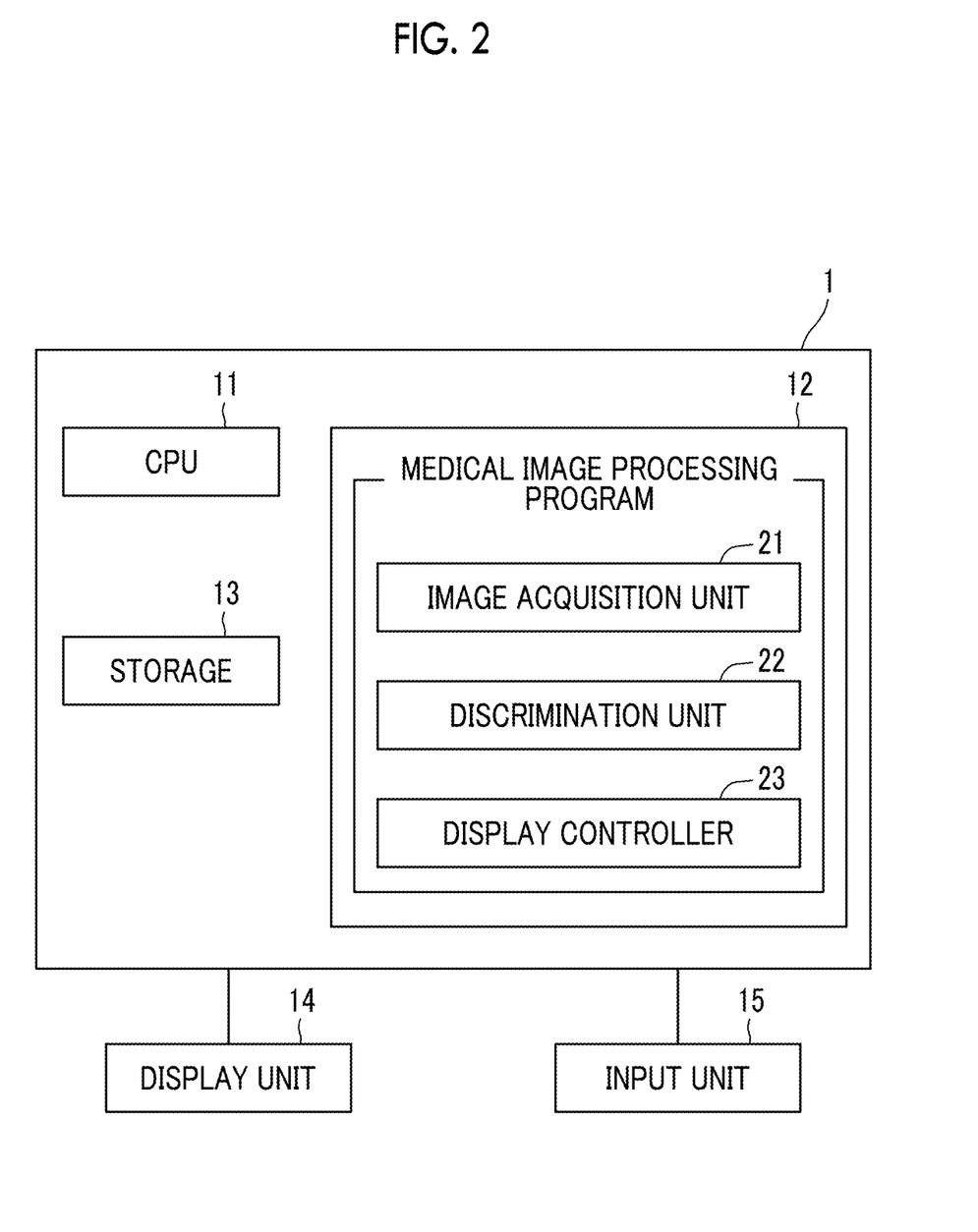
FIG. 2 is a diagram illustrating a schematic configuration of the medical image processing apparatus according to the embodiment of the present disclosure.

FIG. 2 is a diagram illustrating a schematic configuration of the medical image processing apparatus realized by installing the medical image processing program in a computer. As illustrated in FIG. 2, the medical image processing apparatus 1 comprises a central processing unit (CPU) 11, a memory 12, and a storage 13 as a standard workstation configuration. In addition, a display unit 14 such as a liquid crystal display, and an input unit 15 such as a keyboard and a mouse are connected to the medical image processing apparatus 1.

The storage 13 consists of a hard disk drive or the like, and various kinds of information including the brain images of the subject and information required for the process which are acquired from the image storage server 3 via the network 4 are stored.

In the memory 12, the medical image processing program is stored. The medical image processing program defines, as the process executed by the CPU 11, an image acquisition process of acquiring the brain image BO of the subject, a discrimination process of discriminating the disease region included in the brain image BO, and a display control process of displaying the discriminated disease region on the display unit 14.

By the CPU 11 executing those processes according to the program, the computer functions as an image acquisition unit 21, a discrimination unit 22, and a display controller 23.

The image acquisition unit 21 acquires the brain image BO of the brain of the subject from the image storage server 3. In a case where the brain image BO is already stored in the storage 13, the image acquisition unit 21 may acquire the brain image BO from the storage 13.

The discrimination unit 22 discriminates the disease region in the brain image BO. It is assumed that the disease region is a bleeding region in the embodiment. In the embodiment, it is assumed that the discrimination unit 22 is a convolutional neural network (hereinafter, referred to as CNN) which is one of multi-layer neural networks in which a plurality of processing layers are hierarchically connected to each other and deep learning is performed.

Figure 3:
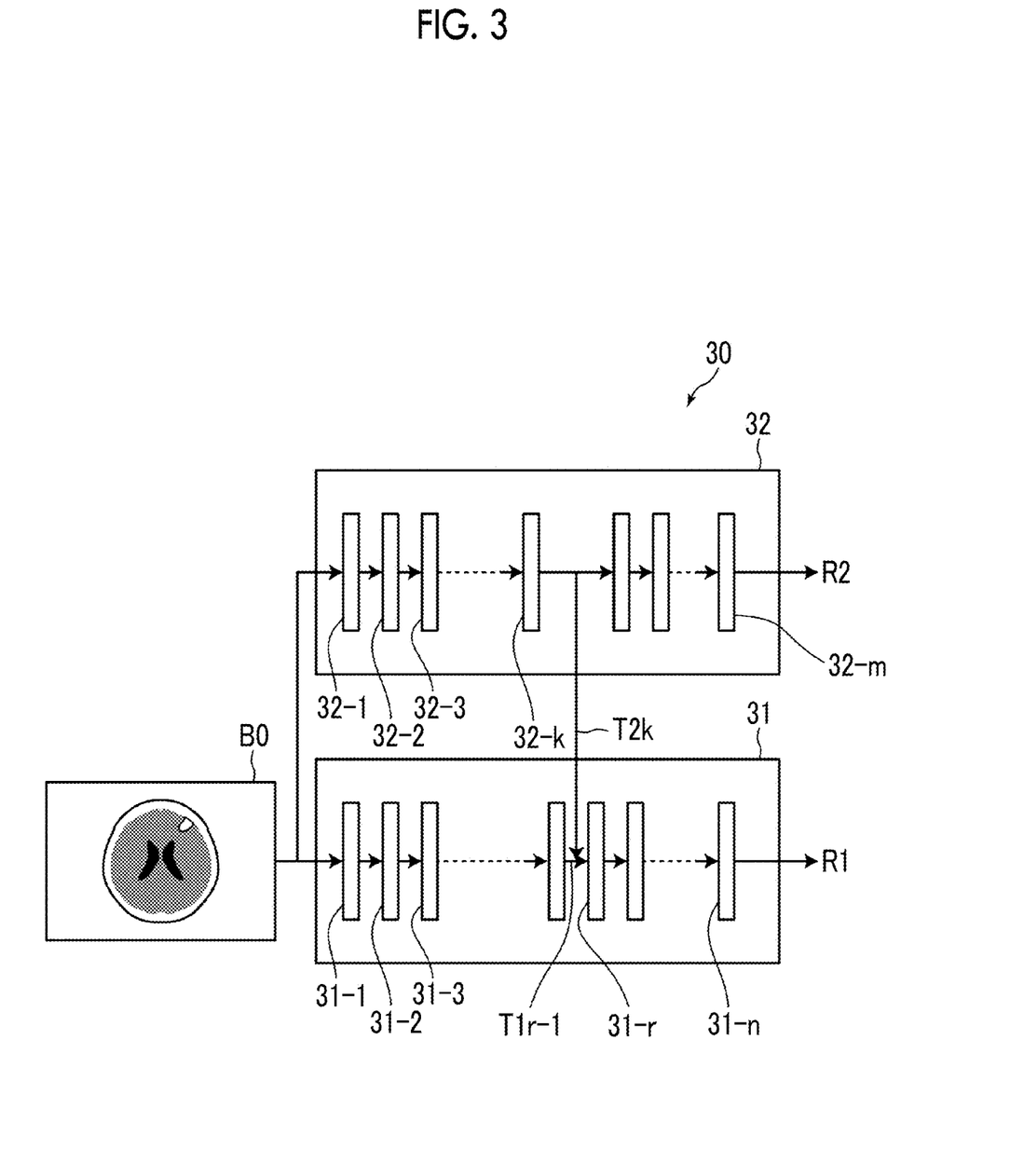
FIG. 3 is a schematic diagram illustrating a configuration of a convolutional neural network in the embodiment.

FIG. 3 is a schematic diagram illustrating a configuration of the CNN in the embodiment. As illustrated in FIG. 3, a CNN 30 has a first neural network 31 and a second neural network 32. The first neural network 31 has a plurality of processing layers 31-1, 31-,2, . . . , 31-$n$ ($n$ is the number of processing layers). Further, the second neural network 32 has a plurality of processing layers 32-1, 32-2, . . . , 32-$m$ ($m$ is the number of processing layers). In the first neural network 31, the first processing layer 31-1 is an input layer and the last processing layer 31-$n$ is an output layer, and in the second neural network 32, the first processing layer 32-1 is an input layer and the last processing layer 32-$m$ is an output layer.

The processing layers of the first neural network 31 and the second neural network 32 consist of convolutional layers or pooling layers. The convolutional layer performs a convolution process using various kernels on the input images, and outputs a feature map consisting of feature quantity data obtained by the convolution process. The kernel has an n×n pixel size (for example, n=3), and a weight is set in each element. Specifically, a weight such as a differential filter for emphasizing the edge of a two-dimensional image such as the brain image BO or the feature map is set. The convolutional layer applies the kernel to the entire feature map output from the brain image BO or the processing layer at the previous stage while shifting the pixel of interest of the kernel. Further, the convolutional layer applies an activation function such as a sigmoid function to the convolved value to output the feature map.

The pooling layer reduces the amount of data of the feature map by pooling the feature map output by the convolutional layer, and outputs the feature map of which the amount of data is reduced.

In the embodiment, the first neural network 31 has performed learning so as to output a discrimination result R1 of the bleeding region for each pixel included in the input brain image by using, as teacher data, multiple brain images including the bleeding region. The bleeding region corresponds to a first medical feature. Accordingly, in a case where the brain image BO is input to the first neural network 31, in the plurality of processing layers 31-$i$ (i=1 to n), the feature map output from the processing layer at the previous stage is sequentially input to the processing layer at the next stage, and the discrimination result R1 of the bleeding region for each pixel in the brain image BO is output from the output layer 31-$n$. The discrimination result R1 output by the first neural network 31 is a result obtained by discriminating whether each pixel of the brain image BO is a bleeding region or a region other than the bleeding region.

The second neural network 32 is different from the first neural network 31, and has learned a task to predict the presence or absence of a disease in the entire brain image BO. The presence or absence of bleeding corresponds to a second medical feature. The second neural network 32 learns to output a discrimination result R2 of whether a bleeding region is included in the input brain image by using, as teacher data, multiple brain images known to include the bleeding region. Accordingly, in a case where the brain image BO is input to the second neural network 32, in the plurality of processing layers 32-$j$ (=1 to m), the feature map output from the processing layer at the previous stage is sequentially input to the processing layer at the next stage, the entire information on the brain image BO is integrated, and the discrimination result R2 of whether the bleeding region is included in the brain image BO is output from the output layer 32-$m$.

The discrimination result R1 of the first neural network 31 includes information on the position of the bleeding region in the brain image BO, but the discrimination result R2 of the second neural network 32 does not include information on the position in the brain image BO since the discrimination result R2 only indicates the presence or absence of the bleeding region.

Here, in the embodiment, a feature map T2$k$ output from the processing layer 32-$k$ in the middle of the second neural network 32 is input to the processing layer 31-$r$ in the middle of the first neural network 31. The feature map T2$k$ includes a feature quantity in which the presence or absence of a bleeding region in the brain image BO is known to some extent. Which processing layer in the first neural network 31 to input the feature map output from which processing layer in the second neural network 32 is designed in advance at the learning stage of the first and second neural networks 31 and 32. The feature map T2$k$ is scaled to have the same size as a feature map T1$r$-1 output from the processing layer 31-$r$-1 at the previous stage of the processing layer 31-$r$, and is input to the processing layer 31-$r$ together with the feature map T1$r$-1. Accordingly, in the embodiment, the first neural network 31 integrates the feature map, which is output from the processing layer in the middle of the second neural network 32, in the processing layer subsequent the processing layer 31-$r$ to output the discrimination result R1 of the local bleeding region in the brain image BO.

Here, depending on the brain image BO, it may be difficult to discriminate the bleeding region only by the local features. Such a bleeding region of the brain image BO can be confirmed in a case where a skilled doctor interprets the brain image BO, but in the discrimination unit using the convolutional neural network or the like, it is difficult to accurately discriminate the bleeding region in some cases. In the embodiment, in the first neural network 31, the discrimination result R1 of the bleeding region is output by integrating the output of the second neural network 32, that is, information on the presence or absence of the bleeding in the brain image BO.

Figure 4:
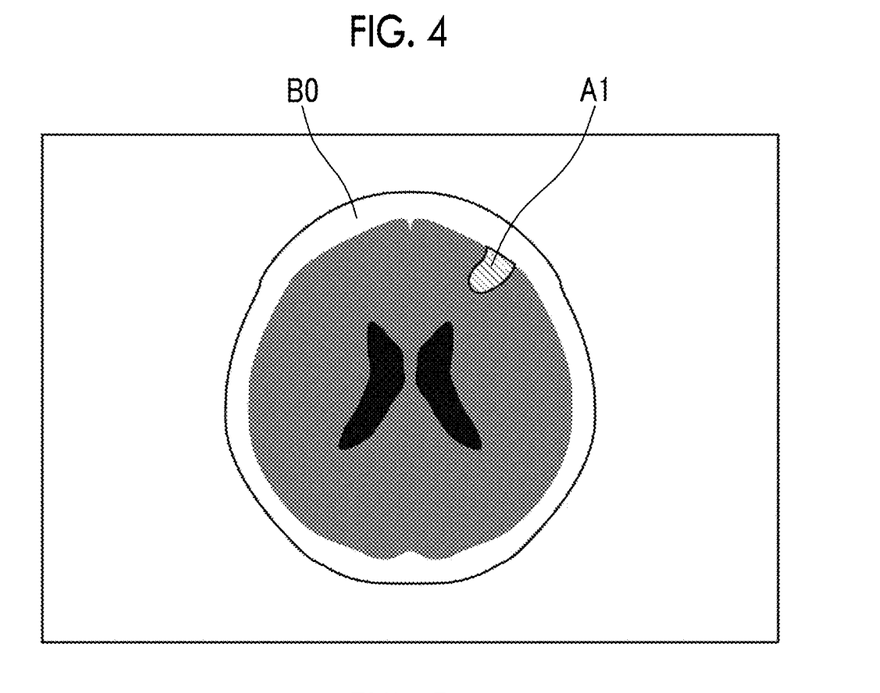
FIG. 4 is a diagram illustrating a brain image in which a bleeding region is specified.

The display controller 23 displays the brain image in which the bleeding region is discriminated on the display unit 14. FIG. 4 is a diagram illustrating the displayed brain image. In FIG. 4, a slice image of one tomographic plane of the brain image BO is illustrated. As illustrated in FIG. 4, a discriminated bleeding region A1 in the brain image BO is highlighted and displayed. For the highlighting, any form can be used such as enclosing the bleeding region A1 with a line, assigning a specific color to the bleeding region A1, or assigning an arrow to the bleeding region A1.

Figure 5:
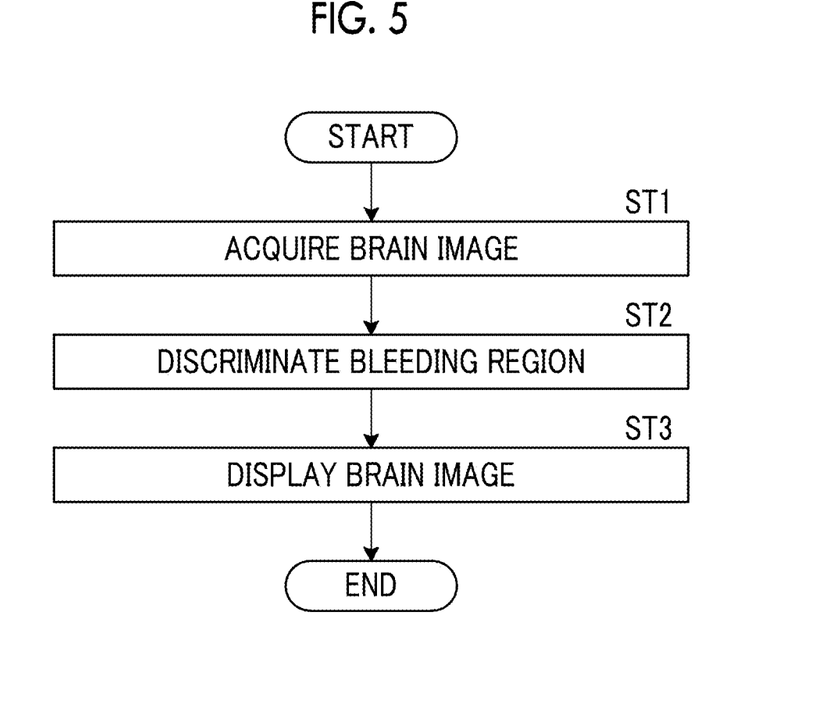
FIG. 5 is a flowchart illustrating a process performed in the embodiment.

Next, the process performed in the embodiment will be described. FIG. 5 is a flowchart illustrating the process performed in the embodiment. First, the image acquisition unit 21 acquires the brain image BO of the subject (Step ST1). Next, the discrimination unit 22 discriminates the bleeding region in the brain image BO (Step ST2), the display controller 23 displays the brain image BO in which the bleeding region is discriminated on the display unit 14 (Step ST3), and the process is ended.

In this manner, in the embodiment, the bleeding region in the brain image BO is discriminated by the first neural network 31 of the discrimination unit 22, and the presence or absence of the bleeding region in the brain image BO is discriminated by the second neural network 32 of the discrimination unit 22. In this case, the feature map T2$k$ output by the processing layer 32-$k$ in the middle of the second neural network 32 is input to the first neural network 31. Therefore, the feature map in the first neural network 31 and the feature map regarding the presence or absence of the bleeding region discriminated by the second neural network 32 are integrated so that the bleeding region in the brain image BO is discriminated in the first neural network 31. Accordingly, according to the embodiment, it is possible to easily and accurately discriminate the bleeding region in the brain image BO.

In the above embodiment, the feature map T2$k$ output by the processing layer 32-$k$ in the middle of the second neural network 32 is input to the first neural network 31, but the discrimination result R2 output by the output layer 32-$m$ of the second neural network 32 may be input to the first neural network 31.

Further, in the above embodiment, the feature map T2$k$ output by the processing layer 32-$k$ in the middle of the second neural network 32 is input to the processing layer 31-$r$ in the middle of the first neural network 31, but the invention is not limited thereto. The feature map T2$k$ output by the processing layer 32-$k$ in the middle of the second neural network 32 or the discrimination result R2 output by the output layer 32-$m$ of the second neural network 32 may be input to the first processing layer 31-1, that is, the input layer of the first neural network 31.

Further, in the above embodiment, the second neural network 32 has learned a task to predict the presence or absence of a bleeding region. However, the task learned by the second neural network 32 is not limited thereto. For example, a task to predict the type of a disease in the brain image BO, for example, bleeding and infarction may be learned. In this case, the second neural network 32 learns to output a discrimination result of the type of included disease (bleeding, infarction, and no disease) in a case where the brain image is input, by using, as teacher data, brain images in which the included disease is known to be either bleeding or infarction.

On the other hand, the bleeding type may be used as the type of a disease. For example, the second neural network 32 may have learned to output a discrimination result of which of intracerebral hemorrhage, intraventricular hemorrhage, subarachnoid hemorrhage, and epidural hemorrhage the bleeding type is. In addition, the second neural network 32 may have learned to discriminate the presence or absence of brain compression findings, or may have learned to discriminate the type of cerebral infarction (acute, old, and the like).

The task learned by the second neural network 32 may be a task to predict clinical findings expressed in the patient as the subject. Here, examples of the clinical findings include a state of consciousness, a state of eye opening, and a state of awakening. In this case, the second neural network 32 learns to output a discrimination result of clinical findings in a case where the brain image is input, by using, as teacher data, the brain image in which the clinical findings are known.

Further, in the above embodiment, the CT image is used as the brain image BO, but the invention is not limited thereto, and other medical images such as the MRI image and the PET image may be used.

Further, in the above embodiment, the brain image BO is used as the medical image, but the invention is not limited thereto. For example, even in a case of discriminating a medical feature included in the medical image, such as the chest, abdomen, whole body, and four limbs of the human body, the present disclosure can be applied.

Further, in the above embodiment, the convolutional neural network is used as the first and second neural networks 31 and 32, but the invention is not limited thereto. As long as the neural network includes a plurality of processing layers, a deep neural network (DNN), a recurrent neural network (RNN), or the like can be used. The first neural network 31 and the second neural network 32 may not be the same neural network. For example, the first neural network 31 may be the convolutional neural network, and the second neural network 32 may be the recurrent neural network.

In the above embodiment, for example, the following various processors can be used as the hardware structure of processing units executing various processes such as the image acquisition unit 21, the discrimination unit 22, and the display controller 23. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (program) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is a form where one processor is configured by a combination of one or more CPUs and software as typified by a computer, such as a client and a server, and this processor functions as a plurality of processing units. Second, there is a form where a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

What is claimed is:

1. A medical image processing apparatus comprising at least one processor, wherein the processor is configured to:
   discriminate a region of a first medical feature included in a medical image by a discrimination unit having a first neural network and a second neural network,
   wherein the first neural network discriminates the first medical feature in the medical image, and consists of a plurality of processing layers,
   wherein the second neural network discriminates a second medical feature associated with the first medical feature, in the medical image, and consists of a plurality of processing layers, and
   a feature quantity output from the processing layer in the middle of the second neural network or an output result of the second neural network is input to the first neural network.

2. The medical image processing apparatus according to claim 1,
   wherein the second neural network has learned a task different from the first neural network.

3. The medical image processing apparatus according to claim 2,
   wherein the task learned by the second neural network is any one of a task to predict presence or absence of a disease, a task to predict a type of a disease, a task to predict clinical findings expressed in a patient, or a task to predict an awareness level of a patient.

4. The medical image processing apparatus according to claim 3,
wherein the first neural network discriminates a local medical feature from the medical image, as the first medical feature, and
the second neural network discriminates a global medical feature from the medical image, as the second medical feature.

5. The medical image processing apparatus according to claim 4,
wherein the medical image includes a brain,
the local medical feature is at least one of a bleeding region or an infarction region of the brain, and
the global medical feature is presence or absence of the at least one of the bleeding region or the infarction region.

6. The medical image processing apparatus according to claim 4, further comprising:
a display controller that displays the medical image in which the local medical feature is specified, on a display unit.

7. The medical image processing apparatus according to claim 1, wherein the medical image is a CT image of a brain.

8. A medical image processing method of discriminating a region of a first medical feature included in a medical image using a discrimination unit, in which the discrimination unit has a first neural network and a second neural network, the medical image processing method comprising:
discriminating the first medical feature in the medical image using the first neural network; discriminating a second medical feature associated with the first medical feature, in the medical image using the second neural network; and
inputting, to the first neural network, a feature quantity output from the processing layer in the middle of the second neural network or an output result of the second neural network.

9. A non-transitory computer-readable storage medium that stores a medical image processing program causing a computer to execute a process of discriminating a region of a first medical feature included in a medical image,
wherein the medical image processing program causes the computer to function as a discrimination unit that has a first neural network and a second neural network,
the medical image processing program causes the computer to execute
a procedure of discriminating the first medical feature in the medical image using the first neural network,
a procedure of discriminating a second medical feature associated with the first medical feature, in the medical image using the second neural network, and
a procedure of inputting, to the first neural network, a feature quantity output from the processing layer in the middle of the second neural network or an output result of the second neural network.

* * * * *